US 6,653,136 B1

(12) United States Patent
Dodgson et al.

(10) Patent No.: US 6,653,136 B1
(45) Date of Patent: Nov. 25, 2003

(54) APPARATUS FOR, AND METHOD OF, INTRODUCING A SUBSTANCE INTO AN OBJECT

(75) Inventors: John Dodgson, Croydon (GB); Anthony R Corless, Ash (GB)

(73) Assignee: Astrazeneca AB, Södertälje (SE)

( * ) Notice: Subject to any disclaimer, the term of this patent is extended or adjusted under 35 U.S.C. 154(b) by 0 days.

(21) Appl. No.: 09/958,755

(22) PCT Filed: Apr. 17, 2000

(86) PCT No.: PCT/GB00/01477

§ 371 (c)(1), (2), (4) Date: Mar. 25, 2002

(87) PCT Pub. No.: WO00/63408

PCT Pub. Date: Oct. 26, 2000

(30) Foreign Application Priority Data

Apr. 16, 1999 (GB) ............................................. 9908681

(51) Int. Cl.⁷ ............................................... C12N 15/64
(52) U.S. Cl. ...................... 435/461; 435/470; 435/471; 435/285.2
(58) Field of Search ................................. 435/461, 470, 435/471, 285.2

(56) References Cited

U.S. PATENT DOCUMENTS

| 4,894,343 | A | | 1/1990 | Tanaka et al. |
| 5,098,843 | A | | 3/1992 | Calvin |
| 5,137,817 | A | | 8/1992 | Busta et al. |
| 5,283,194 | A | | 2/1994 | Schmukler |
| 6,090,617 | A | * | 7/2000 | Meserol ................... 435/285.2 |

FOREIGN PATENT DOCUMENTS

| WO | WO 98/12310 | 3/1998 |
| WO | WO 00 34436 | 6/2000 |
| WO | WO 00/37628 | 6/2000 |

* cited by examiner

Primary Examiner—James Ketter
(74) Attorney, Agent, or Firm—Fish & Richardson P.C.

(57) ABSTRACT

The invention relates to an apparatus for and method of introducing a substance into an object, particularly into a cell or cellular material. In a preferred arrangement apparatus receives the cell and preferably locates it between first and second electrodes and applies a voltage pulse to cause a disruption in the cell wall. This causes the cell to become permeable. The substance may then be introduced, for example under a fluid pressure. Cells may then be inspected and sorted into transfected and non-transfected types. This may be achieved automatically, for example by using electrophoresis.

15 Claims, 7 Drawing Sheets

APPARATUS FOR, AND METHOD OF, INTRODUCING A SUBSTANCE INTO AN OBJECT

This application is the National Phase of International Application PCT/GB00/01477 filed Apr. 17, 2000 which designated the U.S. and that International Application published under PCT Article 21(2) in English.

This invention relates to an apparatus for and method of introducing a substance into an object.

More particularly, but not exclusively, the invention is capable of introducing substances into small objects, such as for example, cellular material or cells. The substance introduced may be a transfecting agent such as: a chemical, molecule, protein, virus, prion or DNA material.

Previously material has been introduced into cells by way of a syringe-like device. These syringe-like devices have to be operated by hand or by complex robotic systems, and in consequence the injection process has been very slow.

The present invention arose to overcome this and other problems associated with syringe-like devices.

It is an object of the invention to increase the efficiency of injection of material into small objects such as cells by the presently-known process of electroporation. In this process cells suspended in a medium are exposed to an electric field sufficiently high to cause the membrane to become permeable. In the present art, cells are suspended in a medium containing the species required to be injected. When the membrane has been made permeable, the species to be injected will either diffuse or be driven by electrophoresis into the cell. After a time the cell membrane will recover from the effects of the pulse and become non-permneable once more. In the present art high concentrations of cells are used, together with macroscopic (ie, with typical minimum dimension of order 100 $\mu$m) electrodes. This means that in general, more than one cell will be in series with each of the field lines in the system—the precise number being random. Hence the field experienced by the cells in the system can very greatly, from below that required for membrane opening, to above that which the cells can stand and remain viable. It is an object of the invention to provide a microfabricated system, with characteristic dimensions considerably smaller than those encountered in presently used electroporation devices, where cells can be electroporated and material injected in conditions which are very similar from cell to cell, allowing uncertainties of field strength and timing to be reduced.

Microfabricated devices for handling, cells and exposing them to electric fields are known. Ayliffe et al (IEEE J MEMS 8(1)50–57 (1999)) show microfabricated channels with micro-electrodes which can be used for electrical impedance measurements on liquids and cells, the latter aimed at detecting the type of cell present and measuring (if possible) some of its properties. The device is not designed for the purpose of electroporation and no mention is made of this. Tanaka et al (U.S. Pat. No. 4,894,343) disclose a microfabricated device for handling cells In wells, designed for the purpose of fusing together two cells located in the same well. Their device comprises an array of wells etched in silicon which are designed to trap the cells, while allowing liquid to move past them through outlets in the bottom of the well. However, the device is not designed to be optimal for electroporation, the present invention uses an improved design.

According to the present invention there is provided an apparatus for introducing a substance into an object comprising: means for introducing the substance to the object; and means for causing permeability of the wall of the object so as to permit said substance to enter said object; characterised in that the means for causing a permeability includes at least one electrode, dimensioned and arranged to form the permeability in the wall of the object upon application of a voltage pulse.

Preferably a characteristic dimension of a channel through, or along, which an object passes or flows is of the order of 50 $\mu$m, more preferably it is less than 30 $\mu$m and most preferably less than 4 times the diameter of the object.

Objects or cells suspended in a liquid medium are introduced into a chamber in which the apparatus(es) is/are located by way of a pump or gravity feed or other suitable fluid displacement mechanism, for example by electro-osmosis.

Preferably at least two electrodes are provided so that the object is located with respect to the electrodes so that a potential difference may be applied in order to render the object wall temporarily permeable.

Means can be provided to restrain or locate the object so that it is positioned with respect to the or each electrode. An advantage of locating the object is that it is positioned in a particular part of a predetermined electric field. Consequently the electric field may be applied with greater precision.

A proximity detector is advantageously included, so that when an object is in the correct location to be in a predetermined part of the electric field, the voltage pulse is applied automatically. Processing means, including electronic logic, may be used to improve and enhance this process.

Preferably there is provided a plurality of the aforementioned apparatuses arranged in an array. An advantage of such an array is that many objects may be acted upon in parallel. This increases throughput.

An array of apparatuses may be formed on a semiconductor substrate, such as for example, silicon or germanium. Proximity detectors, electrodes and processing means may be included on the substrate, for example, in a different layer of an integrated semiconductor structure.

In a particularly preferred embodiment DNA is introduced into living cells by rendering permeable the cell wall by the process of electroporation. DNA then enters the cell from the surrounding medium. Cells are supported in a fluid which is under sufficient pressure to cause cells to move with respect to the electrodes. Means for locating each object with respect to an electrode may comprise a mechanical or electrical structure. An example may be a well or well-like structure, formed for example by back etching a silicon substrate in which the cell locates. A mesh or sieve-like arrangement can be placed at the exit of the well so as to permit passage of fluid but prevent the cell from leaving the well. Preferably a pressure differential established across the substrate urges cells into the well-like structures.

As more cells are located in wells the pressure differential increases because less wells are available, through which fluid may flow. This increased pressure tends to force cells into the wells as they deform relatively easily. One way of preventing this from occurring is to obtain an indication of wells which are occupied and use this information to reduce or increase the pressure differential. This information is readily obtainable as the presence of a cell is known from proximity detectors and a counter in a microprocessor may be used to increment each time a well becomes occupied.

Preferably the apparatus is microfabricated from a biocompatible material. The microfabricated apparatus may include one or more microfabricated channels. These may be formed for example by etching in silicon. Wells or sites for introduction of material may be at a locus in a fluid flow channel.

The channel is preferably narrow, for example, between 1 and 5 times the diameter of the cells (which may typically be around 5–20 μm) to be electroporated. Such narrow channels are advantageous in electroporation, as a greater proportion of the electroporation voltage may be applied across the cell per se, rather than across the cell, any neighbouring cells and the supporting fluid. This enables the field experienced by the cell to be controlled precisely. In an alternative embodiment the channel may even be narrower than the diameter of the cell in its relaxed state. In this embodiment cells deform and flow along the channel and are in closer contact with the walls.

Alternatively the channel or well may be relatively wide except for a constriction in the region at which introduction of material occurs, the constriction, and/or eletroporation electrodes may be designed so that pores, opened in the cell membrane to allow introduction of material, are preferentially oriented at a source of the material.

In a microfabricated device electronic logic may be used to control the amplitude of the electroporation voltage pulse or sequence. The logic circuitry may be integrated within a semiconducting substrate, for example using CMOS, DMOS or bi-polar components, fabricated in a convenient process sequence. Preferably the substrate also forms a support for microfabricated channels. Post-processing techniques can be used during manufacture of the substrate to interconnect electronic components to electrodes in the flow channel(s).

Integration of a moderately high-voltage (typically 5–25 volts although other voltages may be used) switch device (used to control the electroporation voltage) is especially advantageous as the minimal electrical impedance between the switch and the channel may be used to enhance control of the electroporation parameters. The inclusion of one or more capacitive elements adjacent the switch is most preferable as this enhances the ability to source current rapidly without requiring complex current distribution circuitry to the switch. This may be of particular advantage when there is integration of multiple electroporation devices for example in an array. It is an advantage of the present device that as the channels are small, the electrodes can be made close and the voltages needed to achieve electroporation are low and easily controlled.

The introduction of electronic components or logic circuitry, by an active substrate technique, is elegant and is of especial benefit when an array or arrays of electroporation devices are co-fabricated on a common substrate. The possibility exists to substitute or augment such components or circuitry by attaching additional microelectronic components, at appropriate positions, to the substrate. Such components may be attached by surface mount, die and wire bonding, TAB bonding or flip chip bonding. The attachment of devices using conductive adhesive means is especially preferred since this minimises any thermal stresses imparted to the structure during fabrication.

Preferred devices and attachment means and capacitor devices are attached by surface mount (including attachment by conductive adhesives) or by wire bonding. The aforementioned devices are particularly preferred where the substrate is passive or contains low voltage components. Analogue processing circuitry, analogue-to-digital converters, digital signal processing devices, microcomputing or microcontroller elements, and communications devices may also be integrated onto the substrate. The latter devices include optical communication devices. Integration facilitates connection of processing or control circuitry to external processors, such as a microprocessor for closed loop flow control and/or electroporation pulse application.

Preferably sensing means is provided which operates in conjunction with an electrode and a common ground, or a pair of electrodes, to interrogate a channel or well for determining the presence of a cell.

Preferably control means controls the instant of electroporation pulse timing in collaboration with the detection of a cell in the well or channel. For example, a microcontroller, timer or state-machine may be integrated and used to control the instant of application and/or amplitude of an electroporation pulse, in response to a signal indicating the presence of a cell.

Preferably means is provided to determine the state or condition of cells following transfection, indicating whether a cell is unaffected, has had material introduced successfully, or is damaged. For example apparatus as described in published International Patent Application No WO-A-9402846 (BTG) may be utilised for this purpose. Thus it is possible to characterise the cell, at a locus or loci both prior to and following an attempt at introduction of material, and to determine the success or otherwise by the difference in the cell's response rather than by an absolute calibration.

Preferably processing means responds to an external indication of the presence or state of a cell in the electrode vicinity. A trigger may be provided by an operator or automatically by a digital i/o card in a common microcomputer. The trigger may in turn be derived by image processing means such as a video microscope image of the channel.

Detection or monitoring of cells may be done by optical means. Cells may have a fluorescent component introduced into them when material is introduced. This allows automatic fluorescence detection of treated cells, for example by using a video microscope and/or other image processing means, to detect successful introduction. This data may be used to signal the presence of the cell in the electroporation apparatus.

Integrated components or circuitry and an associated well or channel, in the or each electroporation apparatus, are provided with a unique address and a communication means is provided allowing communication to and from a microprocessor. Preferably communication is via a common link or bus.

In the case that the support substrate is silicon the possibility exists to view the cell handling structures through the silicon using suitable infra red radiation. In such an embodiment care must be taken in the layout of the structures to prevent obscuration of the radiation path. An advantage of this embodiment is that the device need not use any member which is optically transmissive in the normal visible band, but is infra red transparent. As infra red radiation may inhibit any fluorescence detection, any infra red detection should be performed at a separate location to fluorescence detection.

Subsequent to the introduction of the material into the cells, there is preferably provided sorting means to direct cells into a collection flow or to a waste flow depending on the result of the introduction. Such sorting may be achieved by a number of methods and include: electrophoresis, dielectrophoresis, "optical tweezers", and/or directed pressure pulses.

Means may be provided to destroy cells which have not been treated in the desired manner. Such destruction may be achieved by killing the cell(s) while leaving it then essentially physically intact or by physically disrupting the cell(s).

Preferred means of achieving this include: electrical disruption of the cell, essentially by overly vigorous electroporation, the introduction of a cell lysing agent; or rapid local heating of the cell or fluid medium in the vicinity of the cell. A micro-heating element or directed, pulsed infra red radiator may be used for this purpose.

In cases where the electroporation apparatus has electrical connections routed about or around it, for example in a highly integrated active substrate, it may be desirable to provide electrical guard bands suitably disposed around portions of the fluid handling structure so that any electric field applied to the fluid is reduced sufficiently so that there is minimal deleterious effect on cells flowing in the channel.

Optical components, such as waveguide optics, may be integrated in processed layers of the substrate which are preferably fabricated in similar processes to those defining fluid channels. Such optical components may include waveguides for interrogation of the cell or support medium in the fluid channel. These may include evanescent field coupling. Alternatively optical components communicate to external signal processing means. Optical components include structures interfacing with fibre optic elements such as etched silicon V-grooves.

Arrays of apparatuses may utilise common external connections for supply of fluids, cells and power supplies and may be imaged in parallel using suitable video microscopy means.

Embodiments of the invention will now be described, by way of examples only, and with reference to the following Figures in which.

Figure 1:
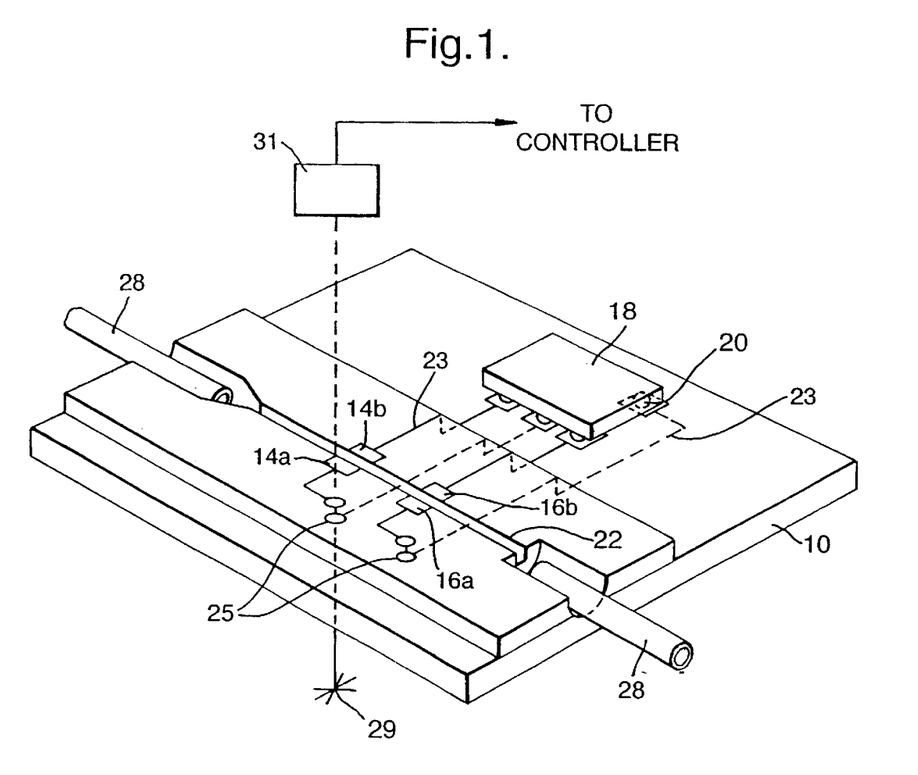
FIG. 1 shows an overall diagrammatical view of one embodiment of an apparatus.

Referring to the Figures, there is shown in FIG. 1 apparatus according to the invention including a substrate 10 which is formed from semiconductor material such as silicon or an insulator such as glass, ceramic or plastic. If formed from a semiconductor material, there may be optionally included CMOS or DMOS or bipolar active devices which are interconnected. Channels 22 are fabricated in the device in order to direct the flow of fluid and cells. An electrode pair 16a and 16b is connected to a voltage supply (not shown) by way of a switch which is activated by the active device. The electrode pair 16a and 16b are preferably formed from gold plated pillars. It is the electrode pair which, when energised with a voltage pulse, make permeable the cell wall so as to permit the introduce of a substance. Optionally electrodes 16a, 16b perform the function of detection of the presence of a cell, by for example variations in capacitance between them. One or more further pairs of electrodes 14a, 14b might be provided in order to detect cells or apply electroporation pulses to them. Contacts to the electrodes are made by tracks 23 and vias 25 as required. It will be appreciated that other means for the detection of cells may be used; for example these may include an optical detector.

Fluid flowing through channel 22 permits the passage of cellular matter supported in the fluid through the electrode configuration. The fluid may pass along the surface of substrate 10 into a plurality of other channels (not shown) whence it is directed to a larger channel or capillary tube for subsequent processing.

Microelectronic logic device 18 may be formed integrally with the substrate material 10 or bonded thereto. Interconnections from device 18 may be by way of conductive glue or solder bumps 20 for example as is achieved in flip chip bonding. A cover plate (not shown) closes channel 22. An optical system including source 29 and detector 31 may be optionally provided for detection or analysis of cells in the channel, for instance to detect whether material has been successfully introduced into the cell. Alternatively optical interrogation might be by means of optical fibres mounted on or to the substrate. Fluid connections to the channel might be made by capillaries 28 inset into receiving grooves, or by other fluidic connection means as known in the art.

Figure 2:
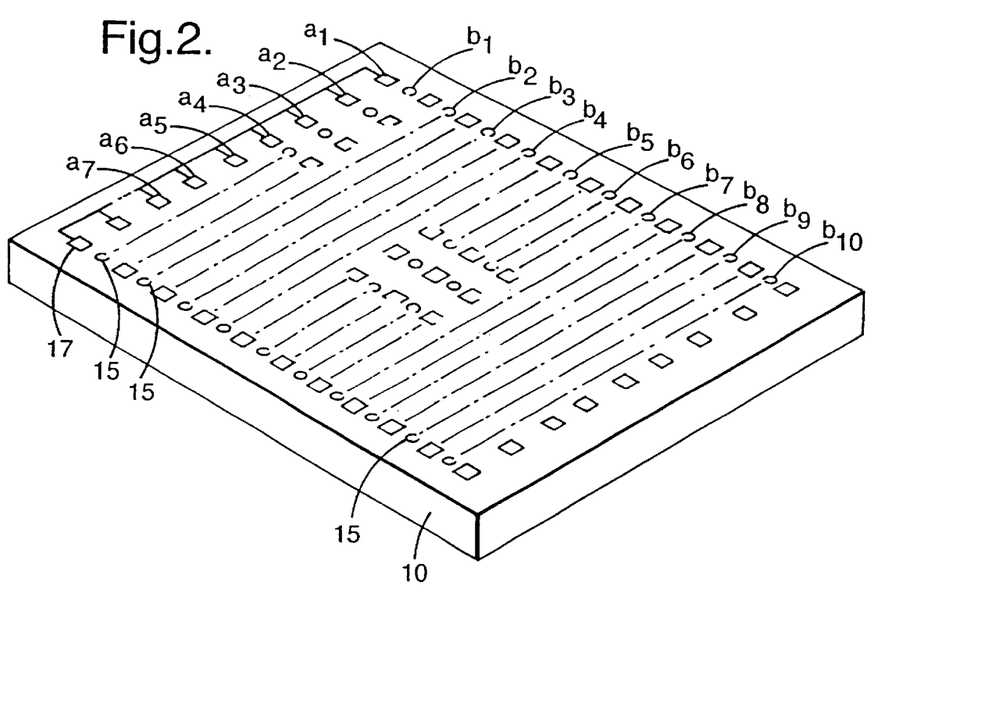
FIG. 2 is an overall general view of a substrate incorporating an array of alternative apparatuses to those shown in FIG. 1.

Alternatively, as shown in FIG. 2, channels may be formed through the substrate. In the embodiment shown in FIG. 2, in which similar features bear the same reference numerals to those in FIG. 1, cells are located in well-like structure 15 and a potential difference is applied to each cell in parallel. The advantage of the embodiment shown in FIG. 2 is that a very large number of cells may be transfected at substantially the same instant. For the purposes of ease of reference small objects are herein referred to as cells. However, the term cell or cells is intended to include small inanimate objects such as particles.

Figure 3:
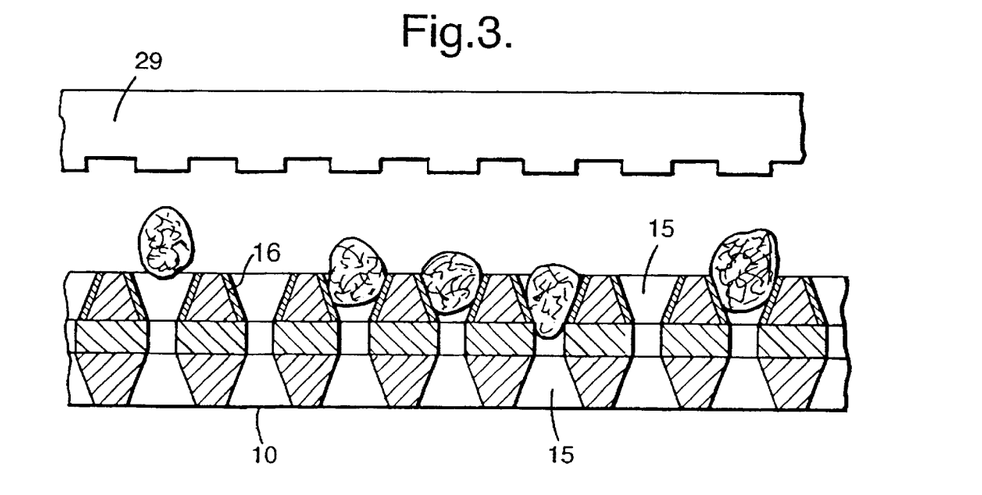
FIG. 3 is a sectional view through the apparatus of FIG. 2.

In the embodiment shown in FIG. 2 and in cross section in FIG. 3 channels are formed through a substrate 10 which have a well like structure 15 on at least one side, the channels being at such a dimension at the base of the well that any cell entering the well is retained in the well, thereby substantially blocking the channel, rather than passing through the channel. The substrate is in contact with two solutions, one above and one below, electrically insulated from one another except at the point of contact within the channels. Cells are located in each well from the solution above the well, for example by a pressure difference across the substrate leading to flow through the channels. The occupancy of the wells might be measured by pressure difference across the substrate, rate of flow through the channels, conductivity through the substrate (which will be approximately equal to the number of open channels) etc. This measurement can also be used to control the location force so as not to deform cells excessively. When the required minimum occupancy of the wells is reached, the cells can be electroporated by applying a voltage pulse between the two solutions. Material to be introduced into the cells might be located in the solution on the opposite side of the substrate from the side to which cells are delivered, and the polarity of the electroporation pulse can be chosen to open the cell membrane and cause material to enter preferentially at this side. In this case the solution sucked through from the front side in localising the cells needs to be removed from the manifold and replaced with one containing the material to be introduced. Alternatively the cells could be suspended in medium containing the material to be introduced and the poration arranged to work preferentially from this side. When the poration process is finished, a reversal of the pressure difference across the substrate can remove the cells from the well, and they can be flowed out of the apparatus (through channels not shown). Optionally, location of the cells in the wells might be achieved by impulse from a shaped moveable sheet member above the substrate, which acts to urge the cells into the wells, for example in FIG. 3 by means of a shaped deformable cover plate 29.

In a particularly preferred embodiment electrodes 16 are mounted on the substrate itself, for example on the upper and lower surfaces, which can act to perform electroporation. The electrode on the upper surface might be segregated into a number of individual electrodes, one for each well or sub-group of wells in the array, such that a cell in an individual well (or group of cells in a group of wells) can be electroporated individually. The electrodes might also be used to detect the presence of a cell in a given well, the coordinates of that well being then noted and the total number of cells counted, the count being used to control the parameters (voltage or current and time) of the electroporation pulse. If necessary, pulses might be applied only to those wells in which there is a cell. This concept differs from that disclosed by Tanaka et al (U.S. Pat. No. 4,894,343) in that in their device, pairs of electrodes are provided in each well, and current is passed between the pair within the well, substantially parallel to the upper surface of the substrate (their FIG. 11). This design is appropriate for their stated aim of fusing two cells present in the well together. The electrode pattern of the present invention, with field passing through the channels substantially perpendicular to the plane of the substrate, will lead to a greater field experienced by the cell and hence greater efficiency of electroporation.

While a silicon wafer is specified in Tanaka et al as being essential to fabrication of their device, in the present invention, any substrate with channels through it can be used, which allows contact between the cells on its surface and solution containing the material to be introduced. Therefore, other materials such as glass and ceramic, synthetic plastics material or insulator-coated metal might also be used.

Figure 4A:
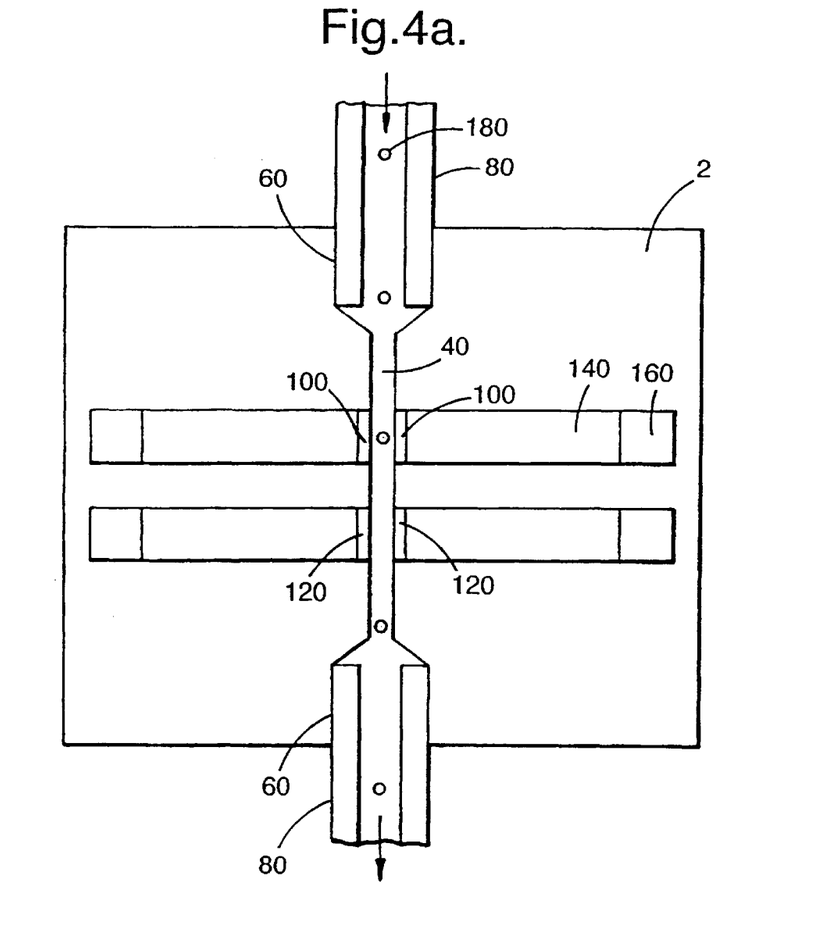
FIGS. 4a–4e and 5 are sections through alternative fluid flow and electrode arrangements showing proximity detectors.

FIG. 4a shows a section through microfabricated device 2, for example made from etched lass, silicon or moulded plastic, which has a flow channel 40. The channel is typically between 1 and 5 times the diameter of the cells which flow through it for transfection. In this embodiment the cells are supported in a medium. Inlet and outlet connection means (recesses, plugs, sockets etc.) 60 are provided which allow capillaries or other hollow connections 80 to be connected to the flow channel. One or more pairs of electrodes 100, 120 are provided in contact with the channel, with electrical connections to external devices via tracks 140 and contacts 160. Electroporation potentials are provided by power supplies not shown. Alternatively, an electrode pair may be configured initially in a detection mode and when a cell is detected, switched into electroporation mode. A series of electrode pairs may be provided to give sequential potential treatments. The electrodes may also be used to measure properties of the cells.

Figure 4B:
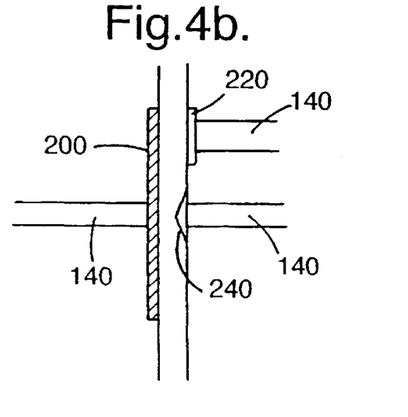

As shown in FIG. 4b the electrodes may use a common around electrode 200 instead of discrete pairs. An electroporation electrode 240 shaped in order to concentrate the field towards the cell or a particular area of the cell may be used. Detection electrodes 220 may be shaped for maximum sensitivity or simply planar. As in FIG. 4c the channel 40 may be close to or even smaller than the diameter of the cells in all or part in order to give close contact between the electrodes and the cell wall.

Figure 4C:
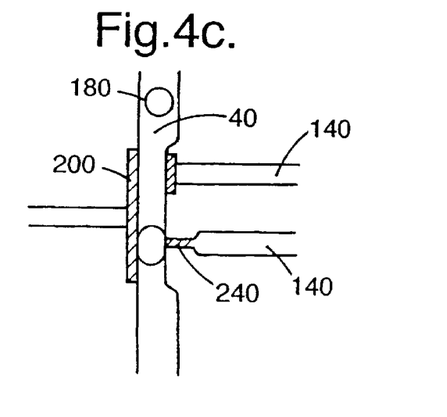

In all the above embodiments the pairs of electrodes may be on the same side of the channel or opposite sides.

Figure 4D:
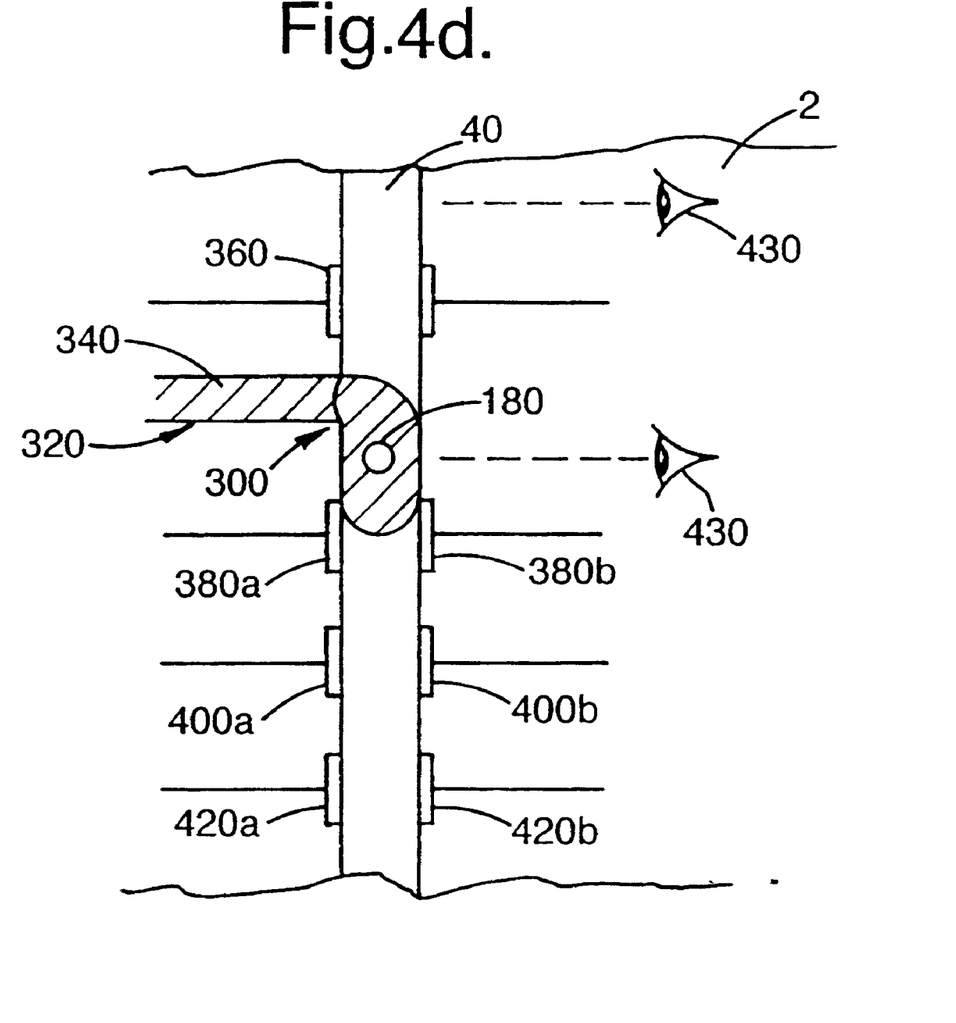

FIG. 4d shows an embodiment in which cells 180 are flowed into flow channel 40 from a supply reservoir not shown, in a carrier medium without the material to be introduced; the device 20 has a junction 300 shown as a T with a second channel 320 for supply of the material 340. Electrodes 380a,b and optionally 400 and 420 are electroporation electrodes. Again these may be discrete pairs or electrodes with a common ground. Again, the electroporation power supply may be a single potential applied to each electrode pair for a given time, or may be a sequence of potentials applied to one or more pairs of electrodes. The material 340 may be flowed continuously into channel 40, or may be applied as a slug only when a cell is present, so enveloping the slug during electroporation. Detection electrodes 360 upstream of the junction may control injection of the material 340 in order to achieve this; electrodes 360 may also control the electroporation process. As in FIG. 4b, electrodes may be shaped in order to enhance the electroporation process. The position of the cell may be monitored optically using detectors (shown diagrammatically as 430) at various stages of the process. Monitoring after the process, for example to check that a fluorescent dye has been introduced into the cell along with the desired material, allows the cells to be sorted according to success or failure of introduction.

Additional side flow channels may be provided to supply to the vicinity of the cell additional materials which assist delivery of the material into the cell. For example, localised chemical poration may be achieved by introduction of an appropriate chemical. This introduction may be transient and under closer control in microfluidic channels so giving advantage over the prior art. Control of the additional introduction may be achieved by electrodes or optical means.

Figure 4E:
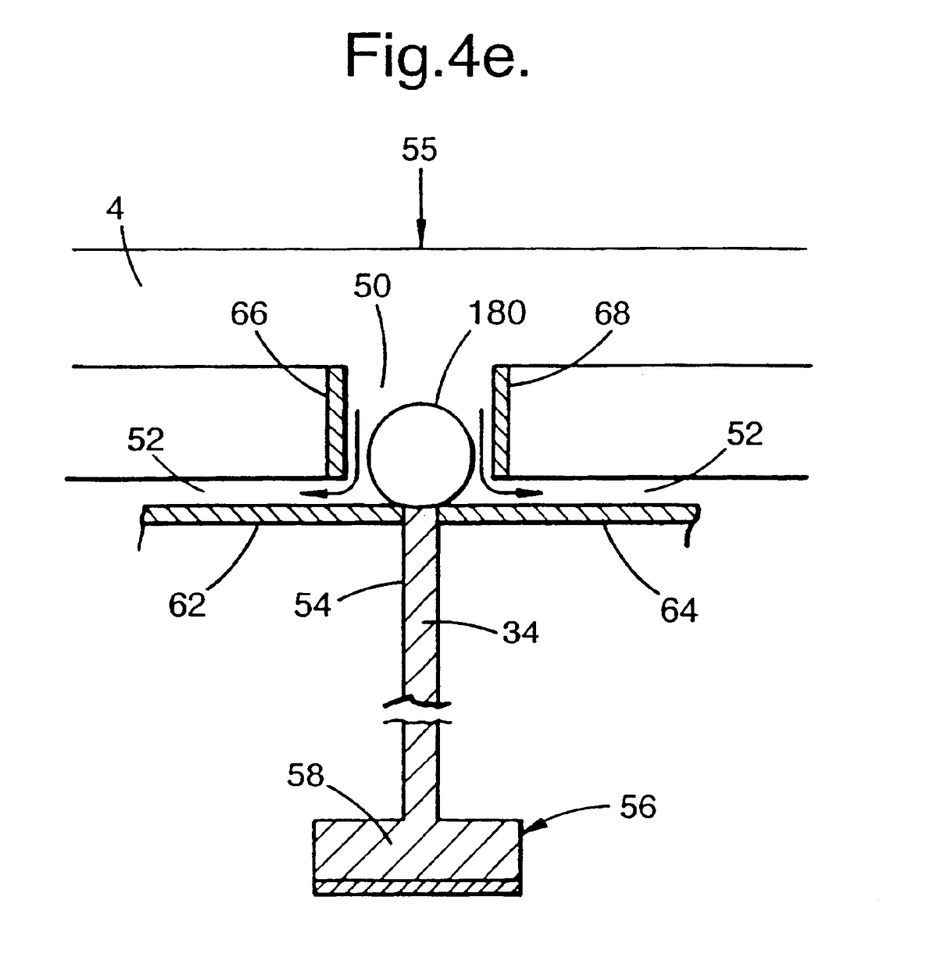

FIG. 4e shows an alternative arrangement to those in FIGS. 4a–d in which pressure applied to cells assists the process of introduction of the material. The cell 180 enters the device along a flow channel 4 entrained in a carrier medium. The cell is captured from this flow by a secondary flow along channels 52 and is localised in well 50. The cell is localised against the orifice of channel 54 which contains the material 34, by a force created by the pressure drop of the flow between channels 4 and 52, or if the cell is a tight fit to the well 50, by a static pressure difference between these channels. Alternatively, the cell may be held in place by physical force from a plunger or deformable section in the top wall 55 of channel 4. A pressure pulse applied to material 34 in channel 54 will then force the material into the cell. The pulse may be applied for example by deformation of a membrane 60 on a chamber 56. The large ratio of area of 60 and the orifice of channel 54 will easily produce a large sudden pressure for injection.

Introduction may be assisted by an electroporation pulse applied between an electrode in contact with material 34, and another in contact with the carrier medium in channel 4. Additional and/or optional electrodes 62, 64 may be provided to electroporate the cell membrane around the orifice of channel 54. Electrodes 62, 64 may also or alternatively be used to detect the presence of the cell in order to initiate or control the process. Electrodes may additionally or alternatively be placed in other positions such as on the sidewalls or around the top of the well 50, e.g. as shown in positions 66, 68, in order to achieve the above.

Figure 5:
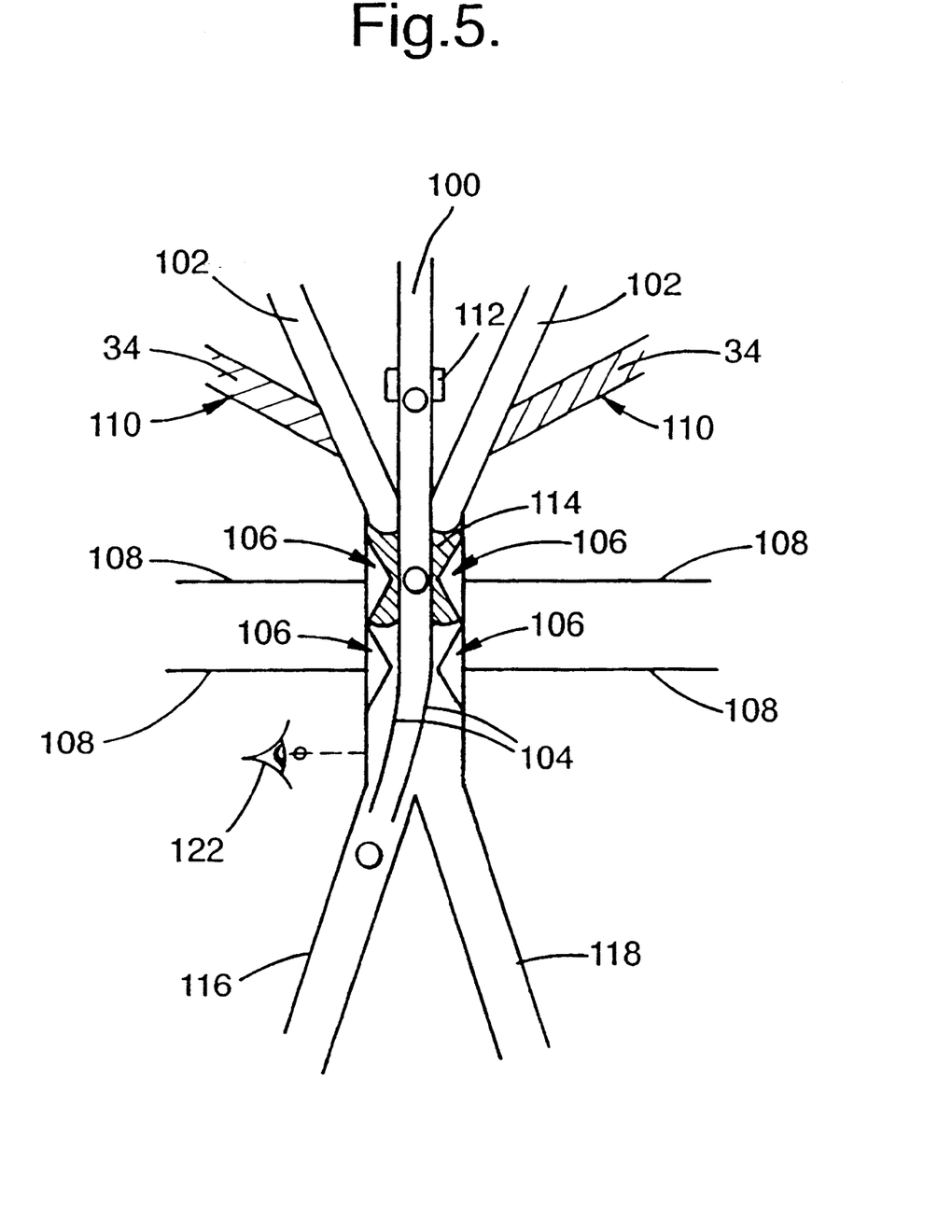

FIG. 5 shows a sheath flow arrangement used to prevent cells adhering to sidewalls and to control their behavior using fluid flow. Cells are introduced to the device through a flow channel 100 which is joined by one or more further channels 102 to provide a sheathing laminar flow, the boundaries between the flows being shown diagrammatically at 104. Electrodes 106 with connections 108 then achieve electroporation. These electrodes may advantageously be shaped in order to concentrate field and / or localise poration. Further pairs of electrodes or other variants as described above may be incorporated. Material 34 to be introduced into cells may be injected into the cell flow down channel 100 as described above, or alternatively may be introduced into the sheath flow, optionally using further channels 110. Material 34 may be-injected as slugs 114 surrounding the cells; control of injection of 34 may be by detection electrodes 112 as before. Success of introduction of material in the cells may be monitored using electrodes or optically (122) as above; more than one outlet 116, 118 may be provided in order for cells to be sorted according to the monitor output. Such sorting processes are well known in the art.

It is understood that while a single site device has been described in the above, the invention is intended to cover-either single or multiple devices, possibly in an array on a common substrate, with separate or common fluidic and electrical connections as may be necessary or advantageous.

Figure 6:
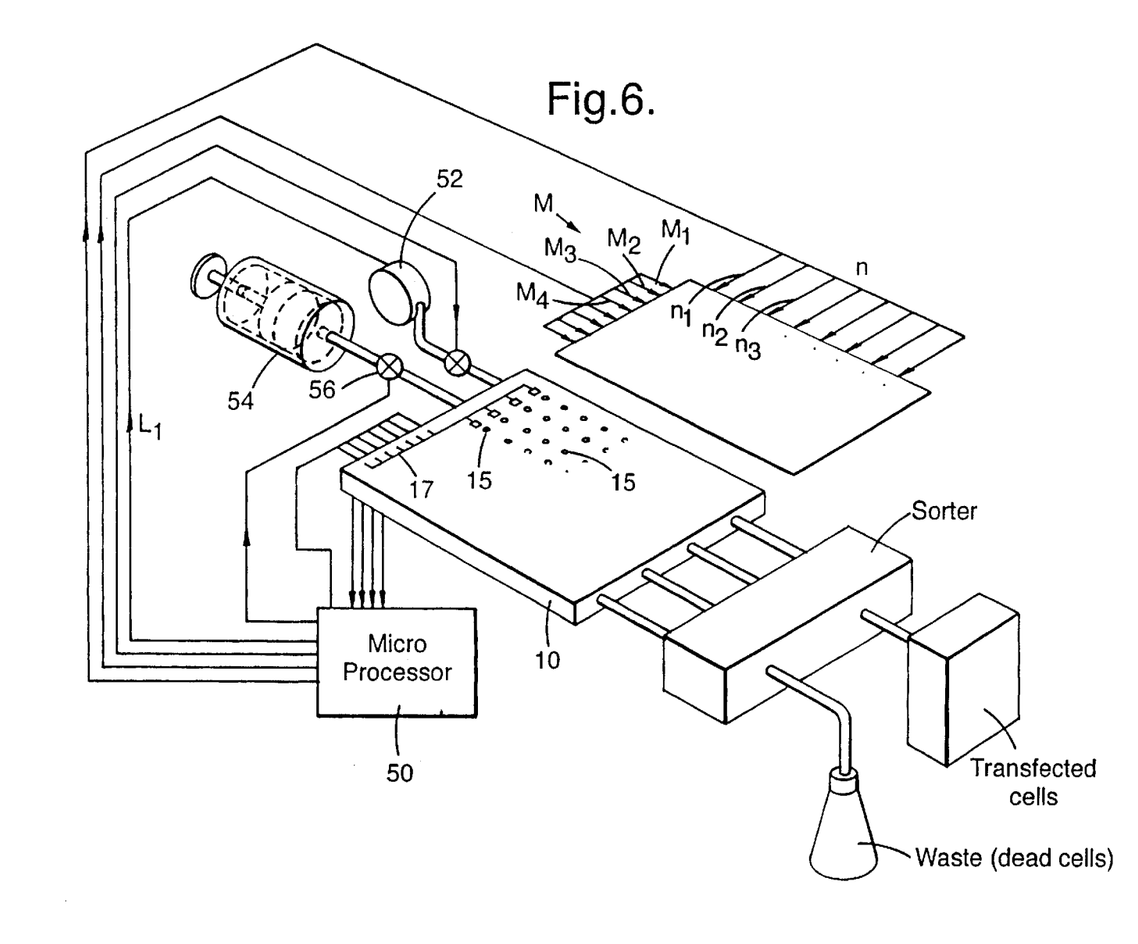
FIG. 6 is an overall view of a system incorporating the invention.

Operation of the invention will now be described by way of overall reference to the figures and specific reference to FIG. 6 which shows a diagrammatical view of a system incorporating the embodiment shown in FIGS. 2 and 3.

Substrate 10 is shown in which the wells 15 are illustrated diagrammatically. Address bus 17 provides a means of interconnecting the data lines from electrodes 16 to a micro processor 50. When a cell is present in well 15, as detected by electrodes 16, a signal indicating this is sent via address bus 17 to microprocessor 50. A separate function performed by the microprocessor increments a counter each time a cell is detected in well 15. Using predetermined look up table and/or an algorithm, the microprocessor sends a signal along line L1 to pump 52. The pump may be replaced by a suitable pressurising means or any suitable mechanism for displacing fluid such as electrostrictive means or electro-osmosis. This signal varies the pressure applied by pump 52 to the fluid present in the apparatus. The reason the fluid pressure is varied is so that as more cells enter wells 15 less pressure is required in order to drive cells into remaining vacant wells. If the pressure was maintained, due to the increase in impedance as wells become occupied, the pressure on one side of the substrate would rise and this would tend to urge cells through the wells. Alternatively or in addition to this a very fine mesh (not shown) or other restrictive means may be applied to the backface of the wells which restrictive means permits the flow of fluid there through but prevent passage of cells. At the end of a cycle the restrictive means may be moved or removed thus permitting the cells to pass through the wells and a fresh charge of cells to be introduced. Cells are stored in a reservoir 54 and are introduced via valve 56 which is under control of the microprocessor 50.

The method will now be described with general reference to all the Figures. A cell 18 passes into well 15 and its presence is detected by proximity detectors. A signal is sent to a counter in microprocessor 50. The counter increments and the value stored therein may be used to modify one or more system parameters, for example pumping pressure. Electroporation then occurs either on the individual cell or simultaneously with one or more other cells.

The invention has been described by way of examples only. It will be understood variation may be made to the examples without departing from the scope of the invention.

What is claimed is:

1. A microfabricated apparatus for introducing a substance into an object comprising: structure that urges the substance and object towards one another so that the substance can enter into the object; and first and second electrodes causing increased permeability of the wall of the object so as to permit said substance to enter said object; said first and second electrodes being; dimensioned and arranged with respect to said structure to create an electric field to permeate in the wall of the object upon application of a voltage pulse, characterized in that application of a voltage pulse is automatic when the object is in a desired position in said electric field to be permeated.

2. The apparatus according to claim 1 wherein said structure includes a channel through which said object passes or flows to a position where it is permeated, the channel is of the order of 50 µm.

3. The apparatus according to claim 1 or 2 having a pump for urging objects into a location at which said voltage pulse is applied.

4. The apparatus according to claim 1 wherein structure is provided to restrain or locate an object in said desired position.

5. The apparatus according to claim 1 having a proximity detector arranged to trigger said voltage pulse when said object is correctly located.

6. The apparatus according to claim 1 formed on a semiconductor substrate.

7. The apparatus according to claim 6 wherein the semiconductor substrate includes silicon.

8. The apparatus according to claim 1 wherein said structure the includes a syringe.

9. The apparatus according to claim 1 including means for determining the state or condition of the object following introduction of the substance.

10. The apparatus according to claim 9, formed on a semiconductor substrate, wherein the semiconductor substrate includes silicon, wherein the means for determining the state or condition of an object includes an optical sensor and an infra-red source.

11. The apparatus according to claim 1 including sorting means arranged to direct transfected objects to a first repository and non-transfected objects to a second repository.

12. A plurality of apparatus, according to claim 1 arranged in an array.

13. A method of introducing a substance into an object comprising the steps of causing the wall of the object to become permeable so as to permit the substance to enter said object, and urging the substance and object towards one another so that the substance enters the object, characterised in that the object is made permeable by subject it to a voltage pulse, the voltage pulse being applied automatically when the object is in a desired position to be permeated.

14. The apparatus of claim 1 wherein a channel is provided through which an object passes or flows to a position where it is permeated, and the channel is less than 30 µm in size.

15. The apparatus of claim 1 wherein a channel is provided through which an object passes or flows to a position where it is permeated, and the channel less than 4 times the diameter of the object.

* * * * *